United States Patent [19]

Shutt

[11] Patent Number: 5,070,063
[45] Date of Patent: Dec. 3, 1991

[54] CATALYST

[75] Inventor: Eric Shutt, Benson, United Kingdom

[73] Assignee: Johnson Matthey Public Limited Company, United Kingdom

[21] Appl. No.: 683,573

[22] Filed: Apr. 10, 1991

Related U.S. Application Data

[63] Continuation of Ser. No. 361,372, Jun. 5, 1989, abandoned.

[30] Foreign Application Priority Data

Jun. 15, 1988 [GB] United Kingdom ............... 8814229

[51] Int. Cl.$^5$ .................................... B01J 27/13
[52] U.S. Cl. ................................ 502/230; 518/715
[58] Field of Search ................................ 502/230

[56] References Cited

U.S. PATENT DOCUMENTS

| 2,900,425 | 8/1959 | Bloch et al. | 502/230 X |
| 2,944,032 | 7/1960 | Nixon | 502/230 X |
| 2,972,649 | 2/1961 | Thomas et al. | 502/230 X |
| 3,017,369 | 1/1962 | Nixon | 502/230 |
| 3,047,514 | 7/1962 | Burr et al. | 502/230 |
| 3,121,696 | 2/1964 | Hoekstra | 502/230 |
| 3,165,479 | 1/1965 | Burk et al. | 502/230 |
| 3,227,658 | 1/1966 | Myers et al. | 502/230 X |
| 3,553,151 | 1/1971 | Giannetti et al. | 502/230 |
| 3,567,796 | 3/1971 | Estes et al. | 502/230 X |
| 3,847,972 | 11/1974 | Kominami et al. | 502/230 X |
| 4,175,056 | 11/1979 | Antos | 502/230 |

FOREIGN PATENT DOCUMENTS

| 0254335 | 1/1988 | European Pat. Off. |
| 2426597 | 1/1975 | Fed. Rep. of Germany |
| 2006261 | 5/1979 | United Kingdom |
| 2074164 | 10/1981 | United Kingdom |

*Primary Examiner*—Patrick P. Garvin
*Attorney, Agent, or Firm*—Stevens, Davis, Miller & Mosher

[57] ABSTRACT

An improved catalyst for the Fischer-Tropsch process, effective at low temperatures and at low catalyst metal loadings on a support, comprises ruthenium and bromine moieties on a support such as gamma alumina.

9 Claims, No Drawings

CATALYST

This application is a continuation of application Ser. No. 361,372, filed June 5, 1989 and now abandoned.

This invention concerns an improved catalyst. More especially it concerns a catalyst for Fischer-Tropsch synthesis, which is a supported ruthenium catalyst.

The Fischer-Tropsch synthesis is a well-established synthetic route from synthesis gas (a mixture of hydrogen and carbon monoxide) to hydrocarbons. There are currently two Fischer-Tropsch plants operating commercially, both operated by SASOL of South Africa and both using iron-based catalysts. It is known that ruthenium-based catalysts are active in the Fischer-Tropsch synthesis (see King et al, Platinum Metals Rev., 1985, 29, (4) 146-154), but for a variety of commercial and technical reasons these have not been used on a commerical scale.

The present invention provides a catalyst for Fischer-Tropsch synthesis, comprising a first component of metallic ruthenium and a second and promoting component of bromine moieties, supported on a third component which is a high surface area support. The support is preferably gamma-alumina, although other alumina or other catalyst supports may be used.

The activity of the catalyst of the invention is such that lower than normally recommended loadings of ruthenium metal can be used, substantially reducing the capital cost of the catalyst. Further advantages accrue from the use of low metal loadings, and it is believed that the low levels of methane formation observed in tests with preferred catalysts can be attributed at least in part to low ruthenium metal loadings. It is also believed that the catalysts of the invention offer a better conversion efficiency than a known ruthenium catalyst of 3 or 4% metal loadings, and this may be observed at relatively low temperature (below 300° C.) Fischer-Tropsch synthesis.

The invention also provides, therefore, the use in a Fischer-Tropsch synthesis of hydrocarbons from hydrogen and carbon monoxide gases, of the catalyst of the invention.

The loading of ruthenium metal on the support is suitably 0.05 to 5%, preferably 0.1 to 2%, most preferably 0.1 to 1%, by weight of the total catalyst. Suitable atomic ratios of bromine to ruthenium are 0.1 to 6.0:1, preferably 1.5 to 4.1.

The catalyst may contain one or more other components; alkali metals or alkaline earth metals, for example potassium, caesium, barium and the like, in metal or ionic form, may be considered.

Preferably, the gamma alumina has a surface area of 50 to 350 $m^2 g^{-1}$, most preferably 150 to 300 $m^2 g^{-1}$.

The process of the invention may be carried out at temperatures of from 150° to 300° C., preferably in the range 180° to 250° C. Conventional pressures of synthesis gas may be used, conveniently in the range 40 to 120 bar, preferably 50 to 100 bar. Conventional gas flow rates may also be used. It is preferred to operate the process using the catalyst in a fixed bed reactor.

The catalyst of the invention may be made by impregnating the support with sources of ruthenium and bromine moieties, for example by the incipient wetness technique or by spraying. The ruthenium and bromine may be deposited in any order or simultaneously. Thereafter, the catalyst is treated as necessary to convert at least a major proportion of the ruthenium present to the metallic form. The source of ruthenium and bromine may be, for example, an aqueous solution of a ruthenium bromide, such as ruthenium tribromide. Other single compounds or complexes may be used.

The invention will now be described by way of example only, in which Examples 1 to 10 are of the invention, and Examples A, B and C are given for comparative purposes.

EXAMPLE 1

So-called "ruthenium tribromide crystal" was made by dissolving ruthenium hydroxide in aqueous hydrobromic acid and evaporating down to leave a residue crystal which comprises mainly ruthenium and bromide moieties possibly contaminated with oxy- or hydroxy-moieties. 54 ml of an aqueous solution of the crystals containing 9.3 g $l^{-1}$ of ruthenium were diluted with distilled water to make 116 ml and the diluted solution was stirred into 200 g of commercial gamma alumina pellets. The pellets were cylindrical extrudates of alumina of diameter 1.59 mm chopped into lengths of from 3 to 10 mm. The quantity of solution added was sufficient to wet thoroughly the surface of the pellets. The wetted pellets were heated to 140° C. for 3 days in an air oven then 33 g of catalyst precursor were loaded into an autoclave basket and the autoclave was heated to 210° C. Wet hydrogen at 1 bar pressure was passed through the autoclave for 30 minutes at a gas hourly space velocity (GHSV) of 500 $hr^{-1}$. (GHSV is the volume of gas passing through the autoclave per hour divided by the volume of the catalyst bed). The hydrogen reduced the ruthenium compounds to ruthenium metal so producing a catalyst system comprising ruthenium metal and bromine moieties supported on gamma-alumina. The catalyst contained bromine and ruthenium in an atomic ratio of 2.75:1 and a ruthenium loading of 0.25 wt % of the catalyst system.

The supported catalyst system was used in the Fischer-Tropsch process as follows:

The hydrogen supply to the autoclave was replaced by a supply of Fischer-Tropsch synthesis gas comprising 58 vol. % hydrogen
29 vol. % carbon monoxide and
13 vol. % argon The argon was used to simulate the presence of the variety of inert gases found in commercial Fischer-Tropsch synthesis gas and to provide a convenient reference for measuring conversion efficiency by gas phase chromatography. The synthesis gas was supplied at a pressure of 61 bar and at an GHSV of 500 $hr^{-1}$. It was found that conversion of over 40% of the carbon monoxide to hydrocarbons could be achieved and only from 0.4 to 2.8% of the converted carbon monoxide was converted to methane, in the temperature interval of 210° to 250° C.

EXAMPLE 2

Example 1 was repeated except that aqueous bromoruthenic acid was used instead of ruthenium bromide crystal dissolved in water.

The catalyst contained bromine and ruthenium in an atomic ratio of 4:1 and the catalyst contained 0.25 wt % ruthenium. It was found that the conversion of carbon monoxide to total hydrocarbons was again over 40% but this time the conversion of carbon monoxide to methane was even lower at 0.4 to 1.3% of the total amount of carbon monoxide converted.

COMPARATIVE EXAMPLE A 4.65 g of bromoruthenic acid solution was diluted to 116 ml in water and used to impregnate 200 gamma-$Al_2O_3$ pellets (1.5 mm extrudate). The impregnated catalyst was dried at 140° C. for 3 days. 50 g of this batch were then reduced in $H_2$ and then tested in the Fischer-Tropsch process according to the procedures of Example 2. It was found that an optimum conversion of CO to total hydrocarbons of 40% was achieved (catalyst A).

A further 50 g of the batch was then washed by adding to it 250 ml of 0.05 molar sodium nitrate solution to remove bromide moieties. The catalyst was allowed to stand for 5 minutes in the solution and then the solution was decanted off and discarded. The washing step was repeated three more times. The catalyst was then reduced in $H_2$ and then tested in the Fischer-Tropsch process according to the procedures of Example 2. It was found that an optimum conversion of CO to total hydrocarbons of only about 22% was achieved (catalyst A1).

The Table shows the pre-test analysis for Ru and Br for these catalysts:

| Catalyst | XRF assays Wt % Ru | Wt % Br | Br/Ru atomic ratio |
|---|---|---|---|
| A | 0.22 | 0.96 | 5.5 |
| A1 | 0.23 | 0.14 | 0.7 |

Clearly, the removal of the bromide moities reduced the efficiency of the catalyst.

COMPARATIVE EXAMPLE B

This example demonstrates the inferior performance of chloride moieties as species for use in a supported ruthenium catalyst system for the Fischer-Tropsch process.

For the purposes of Comparative Example B, 2.93 g of ruthenium as ruthenium trichloride was dissolved in 290 ml of water, and the solution was stirred into 500 g of gamma-alumina pellets. Thereafter the product was dried in an air oven at 105° C. overnight and then reduced using wet hydrogen at 210° C. for two hours before being dried at 105° C. The catalyst was tested in a Fischer-Tropsch process in accordance with the procedure of Example 1 at a temperature of 220° C. and a pressure of 22 bar. It was found that the catalyst system comprised 0.5 wt % ruthenium yet produced only 8.5% conversion of carbon monoxide to hydrocarbons.

COMPARATIVE EXAMPLE C

For the purposes of Comparative Example C, 5 g of ruthenium nitrosyl nitrate ($Ru(NO)(NO_3)_3$) was diluted with water to 58 ml and the solution stirred into 100 g of gamma-alumina pellets. The product was dried in an air oven at 105° C. overnight before being heated to 240° C. for 1 hour to decompose the nitrosyl nitrate to form a catalyst precursor. The precursor was reduced according to the procedure of Comparative Example B and the catalyst system obtained was tested in the Fischer-Tropsch process also in accordance with the procedure of Example 1 at a temperature of 220° C. and a pressure of 22 bar. It was found that the catalyst system contained 0.5 wt % of ruthenium yet produced only 6.5 wt % conversion of carbon monoxide to hydrocarbons.

By comparing Comparative Examples B and C with Examples 1 and 2, it can be seen that substitution of bromide moieties by chloride or nitrogen-containing moieties results in less effective Fischer-Tropsch catalyst systems.

EXAMPLES 3 AND 4

These examples illustrate the effect of a high ratio of bromide moieties to ruthenium on the effectiveness of the catalyst system.

Varying amounts of bromoruthenic acid in 116 mls of distilled water were stirred into 200 g of gamma-alumina pellets as used in Example 1. Both batches of wet pellets were dried at 140° C. for 70 hours in an air oven. The dried pellets were then reduced, analysed for ruthenium and bromine and tested in the Fischer-Tropsch process in accordance with the procedures of Example 1. The results obtained are shown in Table 1.

TABLE 1

| Example | Wt % of Ru in Catalyst | Wt % of Br in Catalyst | Atomic Ratio of Br:Ru | Optimum Conversion of CO to Hydrocarbons % |
|---|---|---|---|---|
| 3 | 0.45 | 1.6 | 4.44 | *40 |
| 4 | 0.47 | 1.0 | 2.66 | 68 |

*Large proportion of methane produced.

It is preferred that the bromide to ruthenium ratio should not exceed about 4:1 and that the minimum ratio should be about 1.5:1.

EXAMPLES 5 TO 10

These examples illustrate the effects of varying the amount of ruthenium in the catalyst.

Various amounts of bromoruthenic acid in either 92.6 ml or 116 ml of distilled water (see Table 2) were stirred into 200 g of gamma-alumina pellets as used in Example 1 except that in the case of Examples 5 to 7 the diameter of the cylindrical extrudate was 1.21 mm. The wet pellets were dried in an air oven at either 190° C. for 18 hours (Examples 5 to 7) or 140° C. for 3 days (Examples 8 to 10) to produce a catalyst precursor. The precursor was then reduced to produce a catalyst and the catalyst was tested in the Fischer-Tropsch process according to the procedures of Example 1. The results obtained are shown in Table 2.

TABLE 2

| Example | Concentration of $HRuBr_4$ used | Wt % Ru in catalyst system | Optimum % CO converted to hydrocarbons | % of Converted CO which is converted to $CH_4$ |
|---|---|---|---|---|
| 5 | 5.25 g in 92.6 ml | 0.35 | 72 | 3.6 |
| 6 | 6.0 g in 92.6 ml | 0.40 | 73 | 4.0 |
| 7 | 7.8 g in 92.6 ml | 0.52 | 78 | 6.4 |
| 8 | 4.65 g in 116 ml | 0.25 | 40 | 1.3 |
| 9 | 9.3 g in 116 ml | 0.50 | 40 | 2.6 |
| 10 | 13.95 g in 116 ml | 0.75 | 64 | 4.4 |

Higher proportions of ruthenium in the catalyst system and finer substrate pellets both favour higher conversions of carbon monoxide to hydrocarbons but they also favour higher conversions of carbon monoxide to methane.

I claim:

1. In a Fischer-Tropsch synthesis catalyst having a first component of ruthenium supported on a second component which is a high surface area catalyst support of gamma-alumina the improvement comprising the use of a third and promoting component of bromine moieties and of the first component being in the form of metallic ruthenium.

2. A catalyst according to claim 1, wherein the gamma-alumina has a surface area of from 50 to 350 $m^2 g^{-1}$.

3. A catalyst according to claim 1, wherein the gamma-alumina has a surface area of from 150 to 300 $m^2 g^{-1}$.

4. A catalyst according to claim 1, wherein the ruthenium is present in an amount of 0.05 to 5% by weight of the total catalyst.

5. A catalyst according to claim 4, wherein the ruthenium is present in an amount of 0.1 to 2% by weight of the total catalyst.

6. A catalyst according to claim 4, wherein the ruthenium is present in an amount of 0.1 to 1% by weight of the total catalyst.

7. A catalyst according to claim 1, wherein the atomic ratio of bromine to ruthenium is from 0.1 to 6:1.

8. A catalyst according to claim 7, wherein the atomic ratio of bromine to ruthenium is from 1.5 to 4:1.

9. A process for the production of a catalyst according to claim 1, comprising impregnating the support component with sources of ruthenium and bromine moieties, and thereafter converting at least a major proportion of the ruthenium present to the metallic form.

* * * * *